United States Patent
Winston

(10) Patent No.: US 12,220,406 B2
(45) Date of Patent: Feb. 11, 2025

(54) COMPOSITIONS FOR THE PREVENTION AND TREATMENT OF METABOLIC SYNDROME

(71) Applicant: Thomas Winston, Stillwell, KS (US)

(72) Inventor: Thomas Winston, Stillwell, KS (US)

(*) Notice: Subject to any disclaimer, the term of this patent is extended or adjusted under 35 U.S.C. 154(b) by 641 days.

(21) Appl. No.: 17/344,078

(22) Filed: Jun. 10, 2021

(65) Prior Publication Data

US 2021/0401812 A1      Dec. 30, 2021

Related U.S. Application Data

(60) Provisional application No. 63/185,796, filed on May 7, 2021, provisional application No. 62/705,116, filed on Jun. 11, 2020.

(51) Int. Cl.

| | |
|---|---|
| A61K 31/436 | (2006.01) |
| A61K 31/155 | (2006.01) |
| A61K 31/232 | (2006.01) |
| A61K 31/352 | (2006.01) |
| A61K 38/22 | (2006.01) |
| A61K 45/06 | (2006.01) |
| A61P 3/04 | (2006.01) |

(52) U.S. Cl.
CPC .......... *A61K 31/436* (2013.01); *A61K 31/155* (2013.01); *A61K 31/232* (2013.01); *A61K 31/352* (2013.01); *A61K 38/22* (2013.01); *A61K 45/06* (2013.01); *A61P 3/04* (2018.01)

(58) Field of Classification Search
CPC .. A61K 31/436; A61K 31/352; A61K 31/155; A61K 38/22; A61K 31/232; A61P 3/04
See application file for complete search history.

(56) References Cited

U.S. PATENT DOCUMENTS 8,461,141 B2 *   6/2013   Hashizume ............. A61P 43/00
                                                          514/183
2014/0155442 A1*  6/2014  Ishida ................... A61K 31/167
                                                          514/513

FOREIGN PATENT DOCUMENTS

CN       105147654 A1     12/2015

OTHER PUBLICATIONS

Marcin Krotkiewski, Thyroid hormones in the pathogenesis and treatment of obesity, European Journal of Pharmacology, vol. 440, Issues 2-3, 2002, pp. 85-98, https://doi.org/10.1016/S0014-2999(02)01420-6 (Year: 2002).*
Gunstad J, Lhotsky A, Wendell CR, Ferrucci L, Zonderman AB. Longitudinal examination of obesity and cognitive function: results from the Baltimore longitudinal study of aging. Neuroepidemiology. 2010;34(4):222-9. doi: 10.1159/000297742. Epub Mar. 18, 2010. PMID: 20299802; PMCID: PMC2883839. (Year: 2010).*
Zhaosha Li, et al., Niacin reduces plasma CETP levels by diminishing liver macrophage content in CETP transgenic mice, Biochemical Pharmacology, vol. 84, Issue 6, 2012, pp. 821-829, ISSN 0006-2952, https://doi.org/10.1016/j.bcp.2012.06.020. (Year: 2012).*
National Center for Biotechnology Information. PubChem Database. Icosapent Ethyl, CID=9831415, https://pubchem.ncbi.nlm.nih.gov/compound/Icosapent-ethyl, accessed on Dec. 22, 2019) (Year: 2019).*
National Center for Biotechnology Information. PubChem Database. Liothyronine, CID=5920, https://pubchem.ncbi.nlm.nih.gov/compound/Liothyronine, accessed on Aug. 21, 2019), (Year: 2019).*
Jordan, V.C., Tamoxifen: A most unlikely pioneering medicine, Nature Reviews: Drug Discovery, vol. 2, 2003, pp. 205-213.*

* cited by examiner

*Primary Examiner* — Kahsay Habte
(74) *Attorney, Agent, or Firm* — Tracey S. Truitt; Sandberg Phoenix & von Gontard, PC

(57) ABSTRACT

Disclosed herein are pharmaceutical compositions to treat or prevent obesity, excess or overweight conditions, and metabolic syndrome comprising an effective amount of one or more mTOR inhibitors and optionally an effective amount of one or more thyroid hormones and/or an effective amount of one or more cholesterol-lowering agents. Further disclosed herein are methods of treating or preventing obesity, excess or overweight conditions, and metabolic syndrome comprising administering an effective amount of a pharmaceutical composition comprising one or more mTOR inhibitors and optionally an effective amount of one or more thyroid hormones and/or an effective amount of one or more cholesterol-lowering agents.

8 Claims, No Drawings

COMPOSITIONS FOR THE PREVENTION AND TREATMENT OF METABOLIC SYNDROME

FIELD

The field of the disclosure relates generally to compositions for the prevention and treatment of obesity, excess or overweight conditions, and metabolic syndrome. More specifically, the field of disclosure relates generally to compositions for the prevention and treatment of obesity, excess or overweight conditions, and metabolic syndrome that include mammalian target of rapamycin (mTOR) inhibitors and optionally an effective amount of one or more thyroid hormones and/or an effective amount of one or more cholesterol-lowering agents.

BACKGROUND

Obesity and excess or overweight conditions are significant problems in the United States and other parts of the world having reached epidemic proportions in recent years with an estimated prevalence of obesity and overweight conditions in adults of about 40%, while childhood obesity and overweight conditions are also high and growing at an alarming rate. These conditions result from a combination of individual factors, including behavioral and genetic factors that result in abnormal or excessive fat accumulation that increases health risks. Factors that can lead to obesity and excess or overweight conditions include certain dietary patterns, general lack of or low level of physical activity, use of certain medications, genetic predisposition, and other issues. Complications associated with obesity and excess or overweight conditions may include poor mental health outcomes, reduced quality of life, and increased risk for metabolic conditions such as hypertension, dyslipidemia, type 2 diabetes, heart disease, or stroke, and other conditions such as gallbladder disease, osteoarthritis, sleep apnea, and some types of cancer. According to the World Health Organization, in 2017 alone over 4 million people died as a result of being overweight or obese.

Metabolic syndrome is often found in association with obesity and excess or overweight conditions. Metabolic syndrome is a condition characterized by the inclusion of at least three of the following five medical issues: 1) Abdominal obesity, 2) High blood pressure, 3) High serum glucose, 4) High triglycerides, and 5) Low serum high-density lipoproteins. Metabolic syndrome is often associated with increased risk of developing cardiovascular disease and Type II diabetes mellitus. Metabolic syndrome is often related to insulin resistance and the diagnosis of prediabetic disease (as measured by hemoglobin A1C) due to multiple factors.

New treatment approaches for obesity, excess or overweight conditions, and metabolic syndrome are needed.

BRIEF DESCRIPTION

Disclosed herein are pharmaceutical compositions for the treatment or prevention of obesity, excess or overweight conditions, and metabolic syndrome comprising an effective amount of one or more mTOR inhibitors and optionally an effective amount of one or more thyroid hormones and/or an effective amount of one or more cholesterol-lowering agents.

In other aspects, disclosed herein are methods of treating or preventing obesity, excess or overweight conditions, and metabolic syndrome comprising administering an effective amount of a pharmaceutical composition comprising one or more mTOR inhibitors and optionally an effective amount of one or more thyroid hormones and/or an effective amount of one or more cholesterol-lowering agents.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the term "patient" refers to a warm blooded animal such as a mammal which is the subject of a medical treatment for a medical condition that causes at least one symptom. It is understood that at least humans, dogs, cats, and horses are within the scope of the meaning of the term. In some aspects, the patient is human. Generally, as used herein, the term "patient" means a human or an animal for which the compositions of the disclosure may be administered.

As used herein, the terms "treat", "treating", and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms encompass also therapy and cure. Treatment may include any manner in which the symptoms of a pathological condition, disorder, or disease are ameliorated or otherwise beneficially altered.

As used herein, the term "prevent" and "preventing" includes administration of a composition which reduces the frequency of, or delays the onset of, or alleviates the symptoms of a medical condition in a subject relative to a subject which does not receive the composition.

As used herein, the term "excess weight" and "overweight" refers generally to conditions characterized by the body mass index (BMI) of a patient at 25 or greater. A patient may also be considered overweight if their weight is above that considered normal or desirable in relation to the patient's height, age, sex, and build, and the patient is at higher risk for health problems than a patient at normal or desirable weight.

As used herein, the term "obese" and "obesity" refers generally to conditions characterized by the BMI of a patient at 30 or greater. A patient may also be considered to be obese if they are more than 20% over their ideal weight based on the patient's height, age, sex, and build, and the patient is at higher risk for health problems than a patient at normal or desirable weight.

As used herein, the term "metabolic syndrome" refers generally to conditions, which are often associated with obesity and overweight conditions that include at least three of the following five medical issues: 1) Abdominal obesity, 2) High blood pressure, 3) High serum glucose, 4) High triglycerides, and 5) Low serum high-density lipoproteins.

As used herein, the term "mTOR complex 1 (mTORC1)" refers to a protein complex comprising mTOR, regulatory-associated protein of mTOR (RAPTOR), mammalian lethal with SEC13 protein 8 (mLST8), proline-rich AKT substrate of 40 kDa (PRAS40) and DEP domain-containing protein 6 (DEPTOR) that has been described to function as a nutrient/energy/redox sensor; regulator of cellular growth, proliferation, and motility; and controller of protein synthesis with roles in inflammation, autophagy and cell survival.

As used herein, the term "mTOR complex 2 (mTORC2)" refers to a protein complex comprising mTOR, mLST8, DEPTOR, rapamycin-insensitive companion of mTOR (RICTOR), mammalian stress-activated protein kinase interacting protein 1 (mSIN1), and protein observed with rictor 1 and 2 (PROTOR1/2) that has been described to function as an activator of insulin receptors and insulin-like growth hormone factor 1 receptors; and regulator of cell proliferation, cell migration and cytoskeletal remodeling with roles in signaling the production of cytokines, inflammation and cell survival.

As used herein, the term "mTOR inhibitor (mTOR Inhibitor)" refers to a composition that either directly or indirectly inhibits one or more functions of mTOR, mTORC1, mTORC2 and combinations thereof. Examples of suitable mTOR inhibitors include omega-3 fatty acid derivatives, biguanide antihyperglycemic agents, flavonoids, macrolides, and other agents that effectively inhibit one or more mTOR protein complex functions.

As used herein, the term "thyroid hormone" refers to a composition that is either equivalent to, a derivative of, or affects the same functions as triiodothyronine (T3). Examples of suitable thyroid hormones include liothyronine.

As used herein, the term "phosphodiesterase 5 inhibitor (PDE5 inhibitor)" refers to a composition that either directly or indirectly inhibits one or more functions of the phosphodiesterase-5 enzyme. Examples of suitable PDE5 inhibitors include tadalafil, sildenafil, vardenafil, and avanafil.

As used herein, the term "cholesterol-lowering agent (CLA)" refers to a composition that either directly or indirectly inhibits the synthesis and/or absorption of cholesterol in the patient. Examples of suitable CLAs include statins, such as atorvastatin, lovastatin, pitavastatin, pravastatin, rosuvastatin, and simvastatin.

Without being bound by theory, it is believed that the pathology of obesity and excess or overweight conditions generally involves excess energy intake in relation to energy consumption; however, genetic predisposition can also be a substantial factor. Additional factors include gene mutations, endocrine disorders, taking certain medications, and psychiatric instability. Treatments include dieting and exercise, certain medications that suppress appetite and/or fat absorption, and bariatric surgeries.

Without being bound by theory, it is also believed that obesity is a major factor in the development of metabolic conditions such as diabetes mellitus, insulin resistance, dyslipidemia, hypertension, and atherosclerosis, which are promoted by the secretion of an excess of inflammatory adipokines. Atherogenic adipokines promote inflammation, insulin-resistance, hypertension, and thrombosis, whereas anti-atherogenic adipocyte hormones are anti-inflammatory. Obesity has been linked to organ dysfunction affecting the heart, liver, lungs, and gastrointestinal, endocrine, and reproductive organs. Obesity is also believed to affect immune dysfunction by the actions of inflammatory adipokines that can disrupt the immune response and increase the risk of certain cancers.

It is generally believed that excess and overweight conditions refer generally to conditions characterized by the BMI of a patient at 25 or greater, whereas obesity refers generally to conditions characterized by the BMI of a patient at 30 or greater. It is also believed that these patients are at higher risk for developing health problems than a patient at normal or desirable weight.

It is believed that a diet that is rich in omega-6 fatty acids compared to omega-3 fatty acids can predispose individuals to obesity and excess or overweight conditions as a result of an increase in the production of pro-inflammatory arachidonic acid-derived eicosanoids. Also, some of the cellular changes believed to occur in obesity and excess or overweight patients is associated with an increase in omega-6 to omega-3 fatty acids in the cellular membranes that may result in an interference with the normal presentation and function of certain membrane-bound receptors including cell bound enzymes, calcium channels, sodium channels, potassium channels and other signaling proteins. As a result, the membrane bound proteins can become less responsive to stimuli including hormones, cell signaling proteins and cell signaling substances, which may in part be due to oxidative stress over time leading to changes in mTOR complex gene regulation and degradation of the omega-3 to omega-6 fatty acid ratio in cellular membranes.

Without being bound by theory, is it also believed that inflammation and improper immune response associated with obesity and excess or overweight conditions is promoted by inflammatory cytokines and other chemicals, some of which are released from cell membranes as a result of an imbalance of the ratio of omega-3 to omega-6 fatty acids and some of which are released from senescent cells that accumulate over time.

Without being bound by theory, it is also believed that mTORC1 and mTORC2 control multiple diffuse aspects of cellular metabolism, cellular integrity, cellular death, immune response and inflammation. It is believed that the mTORC1 and mTORC2 activity is enhanced and driven upwards by cytokine release including those released as a result of higher than optimal ratios of omega-6 to omega-3 fatty acids in the cell membrane and that mTORC1 and mTORC2 complex functions may be down regulated by the use of mTOR inhibitors. Examples of suitable mTOR inhibitors may include omega-3 fatty acid derivatives, biguanide antihyperglycemic agents, flavonoids, macrolides, and other agents that effectively inhibit mTOR protein complexes.

It is further believed that part of the maintenance of the cell membrane may involve maintaining an optimal ratio of omega-3 to omega-6 fatty acids, which results in an anti-inflammatory effect. It is believed that increasing the ratio of omega-3 to omega-6 fatty acids will lead to a decrease or an inhibition of cytokine production. Examples of omega-3 fatty acids include eicosapentaenoic acid (EPA) and docosahexaenoic acid (DHA), which are generally derived from diet. It is believed that EPA is superior to DHA for inhibition of inflammation and maintaining cell integrity. It is believed that omega-6 fatty acids (e.g. arachidonic acids) are precursors to the formation of cytokines. It is believed that omega-3 fatty acids may help to decrease cytokine production, for example, from the action of eicosanoid molecules. Accordingly, a decrease of omega-3 fatty acids, in relation to omega-6, may facilitate an inflammatory response caused by cytokines.

Without being bound by theory, it is believed that therapies including omega-3 fatty acids may downshift cellular signaling by decreasing cytokine formation. This may increase the maintenance of cellular adhesion and normal membrane anatomy with better sodium, potassium and calcium channel function and better response to stimuli from hormones, cell signaling proteins and other cell signaling substances such as nitric oxide. Therapies including omega-3 fatty acids may also facilitate the maintenance of membranes of mitochondria and other intracellular structures. It is also believed that certain CLAs, such as atorvastatin, when dosed in combination with an omega-3 fatty acid derivative, such as icosapent ethyl, may reduce the size of coronary and cerebral artery plaques and reduce the risk of strokes and heart attacks by up to 35% when co-administered in patients for 9 to 18 months.

It is further believed that control over mTOR-associated protein complexes may also be of importance in the treatment and prevention of obesity and excess or overweight conditions. It is believed that mTOR-associated protein complexes may respond to stimuli that alter cellular metabolism and growth. The mTOR-associated protein complexes may be involved in many diseases and almost all tissues of the body, including cancer. It is believed that the dysregulation of mTORC1 and mTORC2 may be an underlying cause of disease over one's lifetime. It is also believed that overactivity of these protein complexes may lead to a higher incidence of obesity and excess or overweight conditions. It is further believed that treatments that include one or more mTOR inhibitors may enhance the treatment and prevention of obesity and excess or overweight conditions.

Without being bound by theory, it is believed that mTOR-associated protein complexes are critical in the regulation of metabolism and inflammation in key metabolic tissues including adipose tissue. It is further believed that excess caloric intake can induce the activation of mTOR-associated protein complex activity, which upon dysregulation may lead to insulin resistance, obesity and excess or overweight conditions.

It is also believed that biguanide antihyperglycemic agents act through inhibition of the mTORC2 complex to modulate cell functions including metabolism, proliferation, migration and survival as well as reduce oxidative stress and inflammation. It is further believed that biguanide antihyperglycemic agents inhibit the mTORC2 complex by mechanisms including the reduction of the downstream effects of the AKT protein that is a component of the PI3K/AKT/mTOR pathway. By reducing the downstream metabolic and inflammatory effects of the PI3K/AKT/mTOR pathway, biguanide antihyperglycemic agents may be effective in treating or preventing obesity and excess or overweight conditions.

Without being bound by theory, it is believed that certain flavonoids act as senolytic agents by reducing mTOR complex activity, increasing the activity of sirtuins, and increasing the activity of AMP-activated protein kinase (AMPK). These actions are believed to play a role in cellular energy homeostasis and promotion of apoptosis in senescent cells that are resistant to signaling proteins and accumulate during the aging process. It is further believed that the accumulation of senescent cells results from a weakened immune system related to aging, and these cells provide a source of chronic inflammation through the release of inflammatory chemicals and may lead to an increased risk of obesity and excess or overweight conditions. It is also believed that the mechanistic actions of certain flavonoids used in combination with a biguanide antihyperglycemic agent can exhibit synergistic effects for promoting apoptosis in senescent cells while promoting homeostasis in normal cells. It is further believed that when certain flavonoids are combined with certain galactomannans, the absorption of the certain flavonoids can be increased by as much as 25-fold.

Without being bound by theory, it is also believed that a combination of anti-inflammatory and senolytic drugs, including mTOR inhibitors, can facilitate the removal of fatty tissue, enhance metabolic activity and improve cellular function, which can lead to greater utilization of calories and less insulin resistance, ultimately resulting in weight loss. It is also believed that a composition comprised of one or more mTOR inhibitors may be more effective if the composition is comprised of at least two or more mTOR inhibitors.

Without being bound by theory, it is believed that the mTOR gene complex 1 and 2, and the metabolism of fats, play large roles in metabolic syndrome. It is believed that aging affects changes resulting in inefficient fat metabolism and a propensity to store excess fat in abdominal adipose tissue. It is also believed that an increase in abdominal adipose tissue increases mTOR activity and inflammation. These changes, along with an increase of growth factors results in an increase of lipoproteins, mainly very low density lipoproteins (VLDLs), which is a contributory risk factor for coronary and other vascular diseases, and can result in decreasing endothelial nitric oxide production, which is believed to result in endothelial dysfunction. Icosapent ethyl is believed to increase beta oxidation of fatty acids, thus increasing Acetyl CoA in the citric acid cycle of the mitochondria. These effects are believed to increase the metabolism of fat to adenosine triphosphate (ATP) in the mitochondria. It is further believed that the effects of icosapent ethyl, therefore, include an increase in fat metabolism under a reduced calorie and reduced carbohydrate diet.

The resulting decrease in mTOR activity by icosapent ethyl is believed to be at least in part through indirect inhibition by increasing beta oxidation, which leads to increased lipid metabolism, which leads to decreased mTOR activity. Decreased mTOR activity can lead to increased senolytic cell death, which causes an increase in lipids, which can cause a repetitive pathway further affecting mTOR activity. The increase in fat metabolism is believed to provide for two effects: reduced requirement for insulin and decreased insulin resistance. Icosapent ethyl is also believed to cause a decrease in triglycerides and VLDLs, especially those made in the liver. The combined effects attributed to icosapent ethyl are believed to result in a decrease in the risk of developing and maintaining metabolic syndrome. Icosapent ethyl is also believed to increase plasma lipoprotein lipase activity, which breaks down triglycerides into fatty acids and glycerol, resulting in subsequent enhancement of lipid metabolism by the citric acid cycle.

It is believed that overeating, with the addition of growth factors, causes an increase in mTOR activity and weight gain. These circumstances are believed to be accompanied by an increase in lipoproteins. Icosapent ethyl is believed to decrease lipoproteins, which decreases mTOR activity by increasing fatty metabolism. Decreasing mTOR activity is also believed to lead to increased senolytic activities including cell death. Cell death further increases lipid availability, which is taken into cells and metabolized to create cellular ATP by the beta oxidation of fatty acids. This promotion of fat metabolism is believed to lead to decreases in weight and fats. These affects are also believed to decrease the need for insulin, because insulin is not stimulated by fats, and reduce insulin resistance associated with weight loss. Thus, icosapent ethyl is believed to act by assisting in the clearance of triglycerides from the blood, decreasing the presence of very low-density lipoproteins by blocking their formation in the liver, and increasing beta oxidation. Icosapent ethyl is also believed to decrease lipogenesis in the liver and increase lipoprotein lipase activity in the serum, which metabolizes fats at least in part by the citric acid metabolic pathway. It is also believed that icosapent ethyl increases the sensitivity to, or amount of production of, endothelial nitric oxide. An increase of nitric oxide sensitivity or production in the endothelial cells is believed to decrease endothelial dysfunction and reduce the onset or severity of hypertension and atherosclerotic and vascular diseases.

Certain flavonoids, including fisetin, acting at least as a senolytic, are believed to enhance the activity of icosapent ethyl by causing cellular breakdown. Fisetin is also believed to affect the PI3K/AKT/mTOR pathway by downregulating the signaling pathway and enhancing lipid metabolism through its senolytic activity leading to cellular death. Therefore, fisetin is also believed to decrease both the need for insulin and insulin resistance. Fisetin is also believed to decrease inflammatory chemical production and/or release in the body, which is expected to decrease the risk of many other diseases associated with or exacerbated by inflammation. Metformin is also believed to lower serum glucose and stimulate the need for increased fat metabolism by blocking gluconeogenesis in the liver.

Thyroid hormones, including e.g. liothyronine (a T3 thyroid hormone), are believed to assist in controlling metabolism by utilizing oxygen and calories for conversion into energy in the mitochondria through the formation of ATP, Thyroid hormones are believed to be necessary for energy production in all organs, especially in muscle, brain, heart, and other tissues. Increased levels of thyroid hormones are believed to affect increased levels of cellular metabolism. Various tests are available to determine thyroid hormone levels, e.g. by measuring the amount of thyroid hormone levels in the blood. Thyroid hormones are believed to enhance the metabolism of fats especially when the body is in a fat-burning mode, using fats for energy. A fat-burning mode may be initiated by withholding glucose either by decreasing carbohydrate intake or decreasing gluconeogenesis with administration of a biguanide antihyperglycemic agent such as metformin. It is further believed that treatment comprising one or more thyroid hormones in combination with fisetin may act synergistically to increase fat metabolism and promote the senolytic effects of fisetin.

Thyroid hormones are believed to affect nearly every cell of the body through receptors in the nucleus of the cell. Thyroid hormones bind to DNA-binding nuclear hormone receptors, cause conformational changes in the receptors, and activate transcription of the thyroid hormone sensitive genes by either initiating expression or upregulation. Also, functions of the PI3K/AKT pathway are believed to include regulation of cell adhesion, cell cycle progression, cell survival and signaling. Precursors to the thyroid hormones, referred to as T4 or thyroxine, are believed to stimulate the PI3/AKT pathway in the cytoplasm, whereas T3 does not. T3 also has a shorter half-life than T4, so T3 is recommended for the treatment of metabolic syndrome over T4.

Inhibition of mTOR1 activity by macrolides, such as rapamycin, is believed to assist in blocking metabolism in cells. It is believed that rapamycin is primarily an mTOR1 inhibitor at lower doses and for short treatment cycles, whereas high levels and very prolonged treatment cycles can also inhibit mTOR2 by blocking mTOR2 production by the cell.

It is believed that treatment regimens that included rapamycin could be most effective and safest if rapamycin is dosed at low levels either intermittently or in conjunction with other mTOR inhibitors and/or additional medications that decrease or down regulate the PI3K-AKT pathway. It is further believed that using a biguanide antihyperglycemic agent, such as metformin, in these treatment regimens will allow for down regulation of both mTOR1 and mTOR2 safely without causing significant side effects of high-dose rapamycin, including insulin resistance, hyperglycemia, immune deficiency, and potentially contribute to the generation of cancer. In addition to acting as an inhibitor of mTOR2, metformin also decreases glycolysis and is effective in controlling blood glucose levels. The addition of a flavonoid, such as fisetin, is believed to provide the added benefit of promoting apoptosis or cell death effectuated at least partly through its inhibition of the mTOR pathway. The effects of fisetin may be further improved with the addition of a T3 thyroid hormone. It is believed that synergy of activity for inhibition of the PI3K-AKT pathway can be achieved with the combination of rapamycin, metformin, and fisetin while providing a low risk of side effects. The treatment regimens could further benefit from the addition of an omega-3 fatty acid derivative, which is believed to downregulate mTOR2, decrease cytokine formation, strengthen cell membranes and structures, and decrease phosphorylation of phosphatides. Additionally, the addition of a T3 thyroid hormone is believed to enhance the effectiveness of the therapy regimen. These combination therapies are believed to have minimal side effects and may be administered continuously over long periods of time.

It is believed that patients with metabolic syndrome may also have endothelial dysfunction. Various tests are available to determine endothelial function including carotid duplex ultrasound, pulse wave velocity, pressure pulsation signal, and acetylcholine endothelial function and adenosine coronary flow reserve tests. It is further believed that patients experiencing endothelial dysfunction associated with metabolic syndrome will benefit from compositions that include the addition of a PDE5 inhibitor. PDE5 inhibitors are believed to increase nitric oxide production in endothelial cells resulting in a decrease in the risk of endothelial dysfunction, reduced risk of atherosclerotic vascular disease, and a decrease in the onset or severity of hypertension.

Without being bound by theory, it is believed that the synthesis of nicotinamide adenine dinucleotide (NAD+), which is at least synthesized from vitamin B3, is decreased as we age and possibly as a result of obesity. NAD+ is believed to have several functions including its role in mitochondrial function and energy production, and as a coenzyme in both β-oxidation and glucose metabolism, including the formation of lactate from pyruvate. It is also believed that metformin inhibits gluconeogenesis and promotes the reduction of body fat by acceleration of the β-oxidative pathway. Omega-3 fatty acids, like icosapent ethyl, are believed to facilitate this metabolic pathway by enhancing the transport and metabolism of fats. It is also believed that NAD+ and adenosine diphosphate ribose have a role in controlling the activity of enzymes involved in cellular homeostasis and DNA repair, including sirtuins and polymerases. Thus, it is believed that administration of NAD+ may help reduce the increased cancer rate that is observed in overweight and obese individuals.

In various embodiments, the compositions of the disclosure include compositions for the treatment of obesity and metabolic syndrome. In various embodiments, the compositions of the disclosure include an effective amount of one or more mTOR inhibitors and optionally an effective amount of one or more thyroid hormones and/or an effective amount of one or more CLAs. In various embodiments, suitable mTOR inhibitors may include omega-3 fatty acid derivatives, biguanide antihyperglycemic agents, flavonoids, and other agents that effectively inhibit mTOR protein complexes. In various embodiments, suitable thyroid hormones may include a T3 hormone, such as liothyronine. In various embodiments, suitable CLAs may include a statin, such as atorvastatin. In various embodiments, the compositions of the disclosure may further include effective amounts of one or more other active agents, such as vitamin B derivatives, quercetin, resveratrol, and NAD+.

Preferentially, at least one of the components of the composition will decrease inflammation associated with obesity, excess or overweight conditions, or metabolic syndrome.

Preferentially, at least one of the components of the composition will decrease the rate of normal cell death or will increase the life span of normal cells including adipocytes and cells involved in immune response systems.

Preferentially, at least one of the components of the composition will enhance cellular membrane integrity and function and/or induce apoptosis in senescent cells. Preferentially, the compositions of the disclosure include a flavonoid, such as fisetin, at doses that are high enough to cause senescent cells to die and results in an overall decrease in inflammation in the patient.

Preferentially, at least one of the components of the composition will enhance cellular metabolism and the conversion of fats into cellular energy.

Preferentially, other than promoting euthyroid in patients, the compositions of the disclosure include a thyroid hormone concurrent with high doses of a flavonoid, such as fisetin.

Preferentially, at least one of the components of the composition will reduce the size of coronary and/or cerebral artery plaques and reduce the risk of stroke and/or heart attack in patients.

Preferentially, the compositions of the disclosure include at least an effective amount of a biguanide antihyperglycemic agent in combination with an effective amount of an omega-3 fatty acid derivative.

In various embodiments, the compositions may include an effective amount of an omega-3 fatty acid derivative. Suitable omega-3 fatty acid derivatives may include icosapent ethyl. In various embodiments, the compositions of the disclosure may include an effective amount of at least about 0.5 g of icosapent ethyl, or between about 0.5 g to about 10.0 g, or 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 g, or any range between any two of these amounts including about 0.5 g to about 10.0 g, or about 1.0 g to about 7.0 g, or about 2.0 g to about 8.0 g. In some preferred forms, the amount of icosapent ethyl is sufficient to maintain an optimum level of icosapent ethyl in the blood of a subject receiving an administration of the composition.

In various embodiments, the compositions of the disclosure may include an effective amount of a biguanide antihyperglycemic agent. Suitable biguanide antihyperglycemic agents include metformin. In various embodiments, the compositions may include an effective amount of at least about 50 mg of biguanide antihyperglycemic agent, or between about 50 mg to about 4000 mg, or 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2025, 2050, 2075, 2100, 2125, 2150, 2175, 2200, 2225, 2250, 2275, 2300, 2325, 2350, 2375, 2400, 2425, 2450, 2475, 2500, 2525, 2550, 2575, 2600, 2625, 2650, 2675, 2700, 2725, 2750, 2775, 2800, 2825, 2850, 2875, 2900, 2925, 2950, 2975, 3000, 3025, 3050, 3075, 3100, 3125, 3150, 3175, 3200, 3225, 3250, 3275, 3300, 3325, 3350, 3375, 3400, 3425, 3450, 3475, 3500, 3525, 3550, 3575, 3600, 3625, 3650, 3675, 3700, 3725, 3750, 3775, 3800, 3825, 3850, 3875, 3900, 3925, 3950, 3975, or 4000 mg or any range between any two of these amounts including about 250 mg to about 4000 mg, about 250 mg to about 500 mg, about 250 mg to about 750 mg, 250 mg to about 1000 mg, about 250 mg to about 1250 mg, about 250 mg to about 1500 mg, or between about 500 mg to about 3000 mg.

In various embodiments, the compositions may include an effective amount of a flavonoid. Suitable flavonoid agents include fisetin and fisetin derivatives. In various embodiments, the compositions may include an effective amount of at least about 10 mg/kg of patient body weight of a flavonoid, or between about 10 mg/kg to about 100 mg/kg of patient body weight, or 10, 15, 20, 25, 30, 35, 40, 45, 50, 55, 60, 65, 70, 75, 80, 85, 90, 95, or 100 mg/kg of patient body weight or any range between any two of these amounts including about 10 mg/kg to about 20 mg/kg, about 15 mg/kg to about 25 mg/kg, about 20 mg/kg to about 30 mg/kg, about 25 mg/kg to about 50 mg/kg, or about 20 mg/kg to about 100 mg/kg of a flavonoid. In some preferred forms, the amount of fisetin is sufficient to maintain an optimum level of fisetin in the blood of a subject receiving an administration of the composition, wherein such optimum level may be achieved by combining the fisetin with a galactomannan to enhance the absorption of the flavonoid.

In various embodiments, the compositions may include an effective amount of a flavonoid. Suitable flavonoid agents include fisetin and fisetin derivatives. In various embodiments, the compositions may include an effective amount of at least about 50 mg of a flavonoid, or between about 50 mg to about 750 mg, or 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750 mg or any range between any two of these amounts including about 50 mg to about 500 mg, about 100 mg to about 750 mg, about 250 mg to about 500 mg, about 250 mg to about 750 mg, about 500 mg to about 750 mg, or about 100 mg to about 500 mg of a flavonoid. In some preferred forms, the amount of fisetin is sufficient to maintain an optimum level of fisetin in the blood of a subject receiving an administration of the composition; such optimum level may be achieved by combining the fisetin with a galactomannan to enhance the absorption of the flavonoid.

In various embodiments, the compositions may include an effective amount of a macrolide. Suitable macrolides include rapamycin. In various embodiments, the compositions may include an effective amount of a macrolide of at least about 0.1 mg of a macrolide, or between about 0.1 mg to about 10 mg, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6. 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6,2, 6.3, 6.4, 6,5, 6.6, 6.7, 6.8, 6.9, 7.0, 7.1, 7.2, 7.3, 7.4, 7,5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mg or any range between any two of these amounts including about 2.0 mg to about 6.0 mg, about 1.0 mg to about 10.0 mg, about 2.0 mg to about 4.0 mg, about 2.5 mg to about 5.0 mg, about 2.5 mg to about 7.5 mg, or about 1.0 mg to about 5.0 mg of a macrolide. In some preferred forms, the amount of rapamycin is administered as a loading dose followed by a lower daily dose. In some preferred forms, the amount of rapamycin is sufficient to maintain an optimum level of rapamycin in the blood of a subject receiving an administration of the composition; such optimum level may be determined as a preferred optimum trough level as measured in nanograms per ml of blood. In some preferred forms, the administration of rapamycin is provided intermittently at low levels.

In various embodiments, the compositions may include an effective amount of a thyroid hormone. Suitable thyroid hormones include the T3 liothyronine. In various embodiments, the compositions of the disclosure may include an effective amount of at least about 1 µg of liothyronine, or between about 1 µg to about 250 µg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 µg, or any range between any two of these amounts including about 5 µg to about 150 µg, or about 10 µg to about 100 µg, or about 10 µg to about 25 µg, or about 25 µg to about 150 µg, or about 25 µg to about 250 µg. In some preferred forms, the amount of liothyronine is sufficient to maintain an optimum level of liothyronine in the blood of a subject receiving an administration of the composition.

In various embodiments, the compositions may include an effective amount of a PDE5 inhibitor. Suitable PDE5 inhibitors include tadalafil, sildenafil, vardenafil, and avanafil. In various embodiments, the compositions of the disclosure may include an effective amount of at least about 1 mg of a PDE5 inhibitor, or between about 1 mg to about 50 mg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg, or any range between any two of these amounts including about 1 mg to about 10 mg, or about 5 mg to about 20 mg, or about 5 mg to about 50 mg, or about 10 mg to about 50 mg, or about 5 mg to about 10 mg of a PDE5 inhibitor. In some preferred forms, the amount of the PDE5 inhibitor is sufficient to maintain an optimum level of a PDE5 inhibitor in the blood of a subject receiving an administration of the composition.

In various embodiments, the compositions may include an effective amount of a cholesterol-lowering agent. Suitable CLAs include atorvastatin, lovastatin, pitavastatin, pravastatin, rosuvastatin, and simvastatin. In various embodiments, the compositions of the disclosure may include an effective amount of at least about 1 mg of a CLA, or between about 1 mg to about 100 mg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg, or any range between any two of these amounts including about 10 mg to about 80 mg, or about 20 mg to about 40 mg, or about 10 mg to about 40 mg, or about 10 mg to about 20 mg, or about 20 mg to about 80 mg of a CLA. In some preferred forms, the amount of a CLA is sufficient to maintain an optimum level of a CLA in the blood of a subject receiving an administration of the composition. In some preferred forms, the effective amount of a CLA, such as atorvastatin, is combined with an effective amount of an omega-3 fatty acid derivative, such as icosapent ethyl, sufficient to maintain an optimum level of both the CLA and the omega-3 fatty acid derivative in the blood of a subject receiving an administration of the composition. In some preferred forms, the effective amount of a CLA, such as atorvastatin, is combined with an effective amount of an omega-3 fatty acid derivative, such as icosapent ethyl, sufficient to reduce the size of coronary and/or cerebral artery plaques and reduce the risk of stroke and/or heart attack of a subject receiving an administration of the composition.

In various embodiments, the compositions may further include an effective amount of a vitamin B derivative. Suitable vitamin B derivatives include nicotinamide riboside. In various embodiments, the compositions include an effective amount of at least about 50 mg of nicotinamide riboside, or about 50 mg to about 1000 mg of nicotinamide riboside, including about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 mg, or any range between any two of these amounts, or about 100 mg to about 750 mg, or about 200 mg to about 500 mg of nicotinamide riboside.

In various embodiments, the compositions further include an effective amount of quercetin. In various embodiments, the compositions may include an effective amount of at least about 100 mg to about 1000 mg, including about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of quercetin.

In various embodiments, the compositions may further include an effective amount of resveratrol. In various embodiments, the compositions may include an effective amount of at least about 100 mg to about 1000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of resveratrol.

In various embodiments, the compositions may further include an effective amount of NAD+. In various embodiments, the compositions may include an effective amount of at least about 100 mg to about 2000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 mg, or any range between any two of these amounts, or about 300 mg to about 1200 mg, or about 300 mg to about 600 mg of NAD+. In various embodiments, the compositions including NAD+ may be further supplemented with adenosine diphosphate ribose.

In various embodiments, the compositions may include an effective amount of a thyroid hormone. Suitable thyroid hormones include the T3 liothyronine. In various embodiments, the compositions may include an effective amount of a combination of one or more thyroid hormones with an effective amount of a flavonoid. In various embodiments, the compositions may include an effective amount of one or more thyroid hormones and an effective amount of a high dose of a flavonoid, which is associated with a senolytic effect.

In various embodiments, the compositions may include an effective amount of a combination of one or more mTOR inhibitors with an effective amount of one or more thyroid hormones. In various embodiments, the compositions may include an effective amount of one or more mTOR inhibitors with an effective amount of one or more thyroid hormones and an effective amount of a flavonoid. In various embodiments, the compositions may include an effective amount of one or more mTOR inhibitors with an effective amount of one or more thyroid hormones and an effective amount of a high dose of a flavonoid, which is associated with a senolytic effect.

In various embodiments, the compositions may include an effective amount of a combination of one or more mTOR inhibitors with an effective amount of one or more CLAs. In various embodiments, the compositions may include an effective amount of one or more mTOR inhibitors with an effective amount of one or more CLAs and an effective amount of one or more thyroid hormones. In various embodiments, the compositions may include an effective amount of one or more mTOR inhibitors with an effective amount of one or more CLAs and an effective amount of one or more thyroid hormones and an effective amount of a flavonoid. In various embodiments, the compositions may include an effective amount of one or more mTOR inhibitors with an effective amount of one or more CLAs and an effective amount of one or more thyroid hormones and an effective amount of a high dose of a flavonoid, which is associated with a senolytic effect.

In various embodiments, the compositions may include an effective amount of a combination of one or more mTOR inhibitors with an effective amount of one or more thyroid hormones and an effective amount of a PDE5 inhibitor. In various embodiments, the compositions may include an effective amount of one or more mTOR inhibitors with an effective amount of one or more thyroid hormones, an effective amount of a flavonoid and an effective amount of a PDE5 inhibitor. In various embodiments, the compositions may include an effective amount of one or more mTOR inhibitors with an effective amount of one or more thyroid hormones, an effective amount of a high dose of a flavonoid, which is associated with a senolytic effect, and an effective amount of a PDE5 inhibitor.

In various embodiments, the compositions of the disclosure may further contain additional pharmaceutically acceptable carriers. The pharmaceutical compositions may, for example, be in a form suitable for oral administration as a tablet, capsule, pill, powder, sustained release formulation, solution or suspension, in a form suitable for parenteral injection as a sterile solution, suspension, or in a form of an emulsion for topical administration as an ointment or cream or for rectal administration as a suppository. The pharmaceutical compositions may be in unit dosage forms suitable for single administration of precise dosages. The pharmaceutical compositions may include conventional pharmaceutical carriers or excipients. In addition, the compositions may include other medicinal or pharmaceutical agents, carriers, adjuvants, etc.

In various embodiments, the compositions may be administered to a patient through any suitable route of administration effective in delivering an amount of active agent or active agents to a patient. Suitable routes of administration include oral, parenteral, enteral, and rectal or the like.

In some forms, the composition will comprise each of the ingredients in a single administration form, such as a pill, tablet, capsule, oral solution, injection solution, infusion solution, or any of the forms described herein. In other forms, the composition may comprise a kit comprising each of the individual ingredients, together with instructions for administering each ingredient. In some forms of the kit, certain ingredients will already be combined such that two, three, or more of the components or ingredients of the composition are in a single administration form as described herein.

Various embodiments of the disclosure further relate to methods of treating or preventing obesity and metabolic syndrome that include administering a composition of an effective amount of one or more mTOR inhibitors and optionally an effective amount of one or more thyroid hormones and/or an effective amount of one or more CLAs. In various embodiments, suitable mTOR inhibitors may include omega-3 fatty acid derivatives, biguanide antihyperglycemic agents, flavonoids, macrolides, and other agents that effectively inhibit mTOR protein complexes. In various embodiments, suitable thyroid hormones may include a T3 hormone, such as liothyronine. In various embodiments, suitable CLAs may include a statin, such as atorvastatin. In various embodiments, the methods of treating metabolic syndrome include administering compositions that further include effective amounts of one or more other active agents, such as vitamin B derivatives, quercetin, resveratrol, and NAD+.

In various embodiments, the methods may include administering an effective amount of an omega-3 fatty acid derivative. Suitable omega-3 fatty acid derivatives may include icosapent ethyl. In various embodiments, the methods may include administering an effective amount of at least about 0.5 g of icosapent ethyl, or between about 0.5 g to about 10.0 g, or 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3,1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 g, or any range between any two of these amounts including about 0.5 g to about 10.0 g, or about 1.0 g to about 7.0 g, or about 2.0 g to about 8.0 g once, twice, or three or more times daily. In some preferred forms, the amount of icosapent ethyl is sufficient to maintain an optimum level of icosapent ethyl in the blood of a subject receiving an administration of the composition.

In various embodiments, the methods may include administering an effective amount of a biguanide antihyperglycemic agent. Suitable biguanide antihyperglycemic agents include metformin. In various embodiments, the methods may include administering an effective amount of at least about 50 mg of biguanide antihyperglycemic agent, or between about 50 mg to about 4000 mg, or 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, 2000, 2025, 2050, 2075, 2100, 2125, 2150, 2175, 2200, 2225, 2250, 2275, 2300, 2325, 2350, 2375, 2400, 2425, 2450, 2475, 2500, 2525, 2550, 2575, 2600, 2625, 2650, 2675, 2700, 2725, 2750, 2775, 2800, 2825, 2850, 2875, 2900, 2925, 2950, 2975, 3000, 3025, 3050, 3075, 3100, 3125, 3150, 3175, 3200, 3225, 3250, 3275, 3300, 3325, 3350, 3375, 3400, 3425, 3450, 3475, 3500, 3525, 3550, 3575, 3600, 3625, 3650, 3675, 3700, 3725, 3750, 3775, 3800, 3825, 3850, 3875, 3900, 3925, 3950, 3975, or 4000 mg or any range between any two of these amounts including about 250 mg to about 4000 mg, about 250 mg to about 500 mg, about 250 mg to about 750 mg, 250 mg to about 1000 mg, about 250 mg to about 1250 mg, about 250 mg to about 1500 mg, or between about 500 mg to about 3000 mg once, twice, or three or more times daily.

In various embodiments, the methods may include administering an effective amount of a flavonoid. Suitable flavonoid agents include fisetin and fisetin derivatives. In various embodiments, the methods may include administering an effective amount of at least about 10 mg/kg of patient body weight of a flavonoid, or between about 10 mg/kg to about 100 mg/kg of patient body weight, or 10, 15, 20, 25, 30, 35, 40, 45, 50, 55, 60, 65, 70, 75, 80, 85, 90, 95, or 100 mg/kg of patient body weight or any range between any two of these amounts including about 10 mg/kg to about 20 mg/kg, about 15 mg/kg to about 25 mg/kg, about 20 mg/kg to about 30 mg/kg, about 25 rag/kg to about 50 mg/kg, or about 20 mg/kg to about 100 mg/kg once, twice, or three or more times daily, weekly, monthly, trimonthly or intermittently with periods between administration when no flavonoid is administered. In some preferred methods, the flavonoid may be administered only one or two days per week, or only one or two days every two weeks, or only one or two days every three weeks or only one or two days per month, bimonthly or trimonthly. In some preferred methods, the flavonoid may be administered each day for two days twice monthly for six months followed by administration one day per month. In various embodiments, the flavonoid or high dose of the flavonoid may include long-term administration, possibly for the life of the patient. In some preferred methods, the amount of fisetin is sufficient to maintain an optimum level of fisetin in the blood of a subject receiving an administration of the composition; such optimum level may be achieved by combining the fisetin with a galactomannan to enhance the absorption of the flavonoid. In various embodiments, a higher dose of fisetin may be associated with a senolytic effect. In various embodiments, a lower dose of fisetin may be associated with an antioxidant effect.

In various embodiments, the methods may include administering an effective amount of a flavonoid that is administered on a daily basis. Suitable flavonoid agents include fisetin and fisetin derivatives. In various embodiments, the methods may include administering an effective amount of at least about 50 mg of a flavonoid, or between about 50 mg to about 750 mg, or 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, or 750 mg or any range between any two of these amounts including about 50 mg to about 500 mg, about 100 mg to about 750 mg, about 250 mg to about 500 mg, about 250 mg to about 750 mg, about 500 mg to about 750 mg, or about 100 mg to about 500 mg once, twice, or three or more times daily. In some preferred methods, the flavonoid may be administered only one or two days per week, or only one or two days every two weeks, or only one or two days every three weeks or only one or two days per month, bimonthly or trimonthly. In some preferred methods, the flavonoid may be administered each day for two days twice monthly for six months followed by administration one day per month. In various embodiments, the flavonoid or high dose of the flavonoid may include long-term administration, possibly for the life of the patient. In some preferred methods, the amount of fisetin is sufficient to maintain an optimum level of fisetin in the blood of a subject receiving an administration of the composition; such optimum level may be achieved by combining the fisetin with a galactomannan to enhance the absorption of the flavonoid. In various embodiments, a higher dose of fisetin may be associated with a senolytic effect. In various embodiments, a lower dose of fisetin may be associated with an antioxidant effect.

In various embodiments, the methods may include administering an effective amount of a macrolide. Suitable macrolides include rapamycin. In various embodiments, the methods may include administering an effective amount of a macrolide of at least about 0.1 mg of a macrolide, or between about 0.1 mg to about 10 mg, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5,5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 mg or any range between any two of these amounts including about 2.0 mg to about 6.0 mg, about 1.0 mg to about 10.0 mg, about 2.0 mg to about 4.0 mg, about 2.5 mg to about 5.0 mg, about 2.5 mg to about 7.5 mg, or about 1.0 mg to about 5.0 mg of a macrolide. In some preferred forms, the amount of rapamycin is administered as a loading dose followed by a lower daily dose. In some preferred forms, the amount of rapamycin is sufficient to maintain an optimum level of rapamycin in the blood of a subject receiving an administration of the composition; such optimum level may be determined as a preferred optimum trough level as measured in nanograms per ml of blood. In some preferred forms, the administration of rapamycin is provided intermittently at low levels.

In various embodiments, the methods may include administering an effective amount of an omega-3 fatty acid derivative in a dosing regimen with an effective amount of a biguanide antihyperglycemic agent.

In various embodiments, the methods may include administering an effective amount of an omega-3 fatty acid derivative in a dosing regimen with an effective amount of a flavonoid.

In various embodiments, the methods may include administering an effective amount of an omega-3 fatty acid derivative in a dosing regimen with an effective amount of a biguanide antihyperglycemic agent and an effective amount of a flavonoid.

In various embodiments, the methods may include administering an effective amount of a biguanide antihyperglycemic agent in a dosing regimen with an effective amount of a flavonoid.

In various embodiments, the methods may include administering an effective amount of a thyroid hormone. Suitable thyroid hormones include liothyronine. In various embodiments, the methods of the disclosure may include administering an effective amount of at least about 1 µg of liothyronine, or between about 1 µg to about 250 µg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 µg, or any range between any two of these amounts including about 5 µg to about 150 µg, or about 10 µg to about 100 µg, or about 10 µg to about 25 µg, or about 25 µg to about 150 µg, or about 25 µg to about 250 µg either weekly, bimonthly, or monthly; however, thyroid hormones should not be given daily and administration should not exceed three days per week. In some preferred methods, the administration of thyroid hormones is dependent upon the clinical response and tolerance of the patient and may continue long-term including many years. In some preferred methods, the amount of liothyronine administered is sufficient to maintain an optimum level of liothyronine in the blood of a subject receiving, an administration of the composition.

In various embodiments, the methods may include diagnosing thyroid functions in each patient prior to administration of an effective amount of a thyroid hormone. In various embodiments, the methods for patients requiring thyroid hormone replacement in order to establish normal thyroid functions may preferentially be administered a T3 thyroid hormone. In various embodiments, patients with normal thyroid functions may be administered a low dose of a T3 thyroid hormone (e.g. 5 to 10 µg of liothyronine) combined with a high dose of a flavonoid. In various embodiments, the methods may include administering a combination of a low dose of a T3 thyroid hormone and a high dose of a flavonoid that effectively elicits a synergistic effect of increasing fat metabolism and promoting cellular senescence. In various embodiments, other than promoting euthyroid in patients, the methods include administering a thyroid hormone concurrent with high doses of a flavonoid, such as fisetin.

In various embodiments, the methods may include administering an effective amount of a PDE5 inhibitor. Suitable PDE5 inhibitors include tadalafil, sildenafil, vardenafil, and avanafil. In various embodiments, the methods of the disclosure may include administering an effective amount of at least about 1 mg of a PDE5 inhibitor, or between about 1 mg to about 50 mg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg, or any range between any two of these amounts including about 1 mg to about 10 mg, or about 5 mg to about 20 mg, or about 5 mg to about 50 mg, or about 10 mg to about 50 mg, or about 5 mg to about 10 mg of a PDE5 inhibitor once, twice, or three or more times daily. In some preferred methods, the effective amount of a PDE5 inhibitor is dosed in a range that is based on each specific PDE5 inhibitor's preferred dosing range for the treatment of pulmonary hypertension. For example, the effective amount of the PDE5 inhibitor, tadalafil, would be administered at a dose in the range of about 5 mg to about 10 mg. In some preferred methods, the amount of a PDE5 inhibitor is sufficient to maintain an optimum level of a PDE5 inhibitor in the blood of a subject receiving an administration of the composition. In various embodiments, the methods may limit the administration of a PDE5 inhibitor to patients that experience endothelial dysfunction.

In various embodiments, the methods may include administering an effective amount of a cholesterol-lowering agent. Suitable CLAs include atorvastatin, lovastatin, pitavastatin, pravastatin, rosuvastatin, and simvastatin. In various embodiments, the methods of the disclosure may include administering an effective amount of at least about 1 mg of a CLA, or between about 1 mg to about 100 mg, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg, or any range between any two of these amounts including about 10 mg to about 80 mg, or about 20 mg to about 40 mg, or about 10 mg to about 40 mg, or about 10 mg to about 20 mg, or about 20 mg to about 80 mg of a CLA once, twice, or three or more times daily and may continue long-term including many months. In some preferred methods, the amount of a CLA administered is sufficient to maintain an optimum level of a CLA in the blood of a subject receiving an administration of the composition. In some preferred methods, administration of the effective amount of a CLA, such as atorvastatin, is combined with an effective amount of an omega-3 fatty acid derivative, such as icosapent ethyl, sufficient to maintain an optimum level of both the CLA and the omega-3 fatty acid derivative in the blood of a subject receiving an administration of the composition. In some preferred methods, administration of the effective amount of a CLA, such as atorvastatin, is combined with an effective amount of an omega-3 fatty acid derivative, such as icosapent ethyl, sufficient to reduce the size of coronary and/or cerebral artery plaques and reduce the risk of stroke and/or heart attack of a subject receiving an administration of the composition.

In various embodiments, the methods may include administering an effective amount of a vitamin B derivative. Suitable vitamin B derivatives include nicotinamide riboside. In various embodiments, the methods may include administering an effective amount of at least about 50 mg of nicotinamide riboside, or about 50 mg to about 1000 mg of nicotinamide riboside, including about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, and 1000 mg, or any range between any two of these amounts, or about 100 mg to about 750 mg, or about 200 mg to about 500 mg nicotinamide riboside once, twice, or three or more times daily.

In various embodiments, the methods may include administering an effective amount of quercetin. In various embodiments, the methods may include administering an effective amount of at least about 100 mg to about 1000 mg, including about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of quercetin once, twice, or three or more times daily.

In various embodiments, the methods may include administering an effective amount of resveratrol. In various embodiments, the methods may include administering an effective amount of at least about 100 mg to about 1000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 mg, or any range between any two of these amounts, or about 100 mg to about 750 mg, or about 200 mg to about 500 mg of resveratrol once, twice, or three or more times daily.

In various embodiments, the methods may include administering an effective amount of NAD+. In various embodiments, the methods may include administering an effective amount of at least about 100 mg to about 2000 mg, or about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 mg, or any range between any two of these amounts, or about 300 mg to about 1200 mg, or about 300 mg to about 600 mg of NAD+ once, twice, or three or more times daily. In various embodiments, the methods that include administering NAD+ may be further supplemented with adenosine diphosphate ribose. In various embodiments, the methods may include administering NAD+ at a lower daily dose when it is administered in combination with a high dose of fisetin and T3, such lower dose of NAD+ being about half of the dose administered otherwise.

In various embodiments, the methods may include administering an effective amount of a combination of thyroid hormones. Suitable thyroid hormones that may be included in the combination include the T3 liothyronine. In various embodiments, the methods may include administering an effective amount of a combination of one or more thyroid hormones with an effective amount of a flavonoid. In various embodiments, the methods may include administering an effective amount of one or more thyroid hormones and an effective amount of a high dose of a flavonoid, which is associated with a senolytic effect. In various embodiments, the methods may include administering a combination of an effective amount of one or more thyroid hormones with either an effective amount of a flavonoid or a high dose of a flavonoid, wherein only some of the compositions that include an effective amount of a flavonoid also include an effective amount of one or more thyroid hormones. For example, an effective amount of one or more thyroid hormones may be included only in one of two weekly compositions administered that includes an effective amount of a flavonoid or a high dose of a flavonoid, which composition could be either the first or second weekly composition administered that includes a flavonoid or high dose flavonoid.

In various embodiments, the methods may include administering an effective amount of a combination of one or more mTOR inhibitors with an effective amount of one or more thyroid hormones. In various embodiments, the methods may include administering an effective amount of one or more mTOR inhibitors with an effective amount of one or more thyroid hormones and an effective amount of a flavonoid. In various embodiments, the methods may include administering an effective amount of one or more mTOR inhibitors with an effective amount of one or more thyroid hormones and an effective amount of a high dose of a flavonoid, which is associated with a senolytic effect. In various embodiments, the methods may include administering a combination of an effective amount of one or more mTOR inhibitors with an effective amount of one or more thyroid hormones and either an effective amount of a flavonoid or a high dose of a flavonoid, wherein only some of the compositions that include an effective amount of a flavonoid also include an effective amount of one or more thyroid hormones. For example, an effective amount of one or more thyroid hormones may be included only in one of two weekly compositions administered that includes an effective amount of a flavonoid or a high dose of a flavonoid, which composition could be either the first or second weekly composition administered that includes a flavonoid or high dose flavonoid. In various embodiments, the one or more thyroid hormones should be administered for short durations (for example, two days a week, bimonthly, or monthly) during any periods of a dosing regimen that include a high dose of a flavonoid.

In various embodiments, the methods may include administering an effective amount of a combination of one or more mTOR inhibitors with an effective amount of one or more CLAs. In various embodiments, the methods may include administering an effective amount of one or more mTOR inhibitors with an effective amount of one or more CLAs and an effective amount of one or more thyroid hormones. In various embodiments, the methods may include administering an effective amount of one or more mTOR inhibitors with an effective amount of one or more CLAs and an effective amount of one or more thyroid hormones and an effective amount of a flavonoid. In various embodiments, the methods may include administering an effective amount of one or more mTOR inhibitors with an effective amount of one or more CLAs and an effective amount of one or more thyroid hormones and an effective amount of a high dose of a flavonoid, which is associated with a senolytic effect.

In some preferred forms, the methods include administering a macrolide, such as rapamycin; in combination with a biguanide antihyperglycemic agent, such as metformin; in combination with an omega-3 fatty acid derivative, such as icosapent ethyl; in combination with a flavonoid, such as fisetin; and in combination with a T3 thyroid hormone, such as liothyronine. In some preferred forms, the methods include administering a macrolide, such as rapamycin, dosed weekly to achieve blood levels below specified levels measured at specified times following administration; in combination with a biguanide antihyperglycemic agent, such as metformin, dosed twice daily; in combination with an omega-3 fatty acid derivative, such as icosapent ethyl, dosed twice daily; in combination with a flavonoid, such as fisetin, dosed daily; in combination with a T3 thyroid hormone, such as liothyronine, dosed either for two days in a row per week or dosed on separate days for no more than 3 days per week. In some preferred forms, the methods include administering a macrolide, such as rapamycin, dosed weekly to achieve blood levels below about 12 nanograms per ml of blood measured at about 60 hours plus or minus 3 hours following administration; in combination with a biguanide antihyperglycemic agent, such as metformin, dosed twice daily at about 500 mg to about 2000 mg; in combination with an omega-3 fatty acid derivative, such as icosapent ethyl, dosed twice daily at about 2.0 g to about 4.0 g; in combination with a flavonoid, such as fisetin, dosed daily at about 20.0 mg/kg patient body weight (which dose may be achieved by starting at a daily dose of about 200 mg and stepping up to the daily dose of about 20.0 mg/kg); in combination with a T3 thyroid hormone, such as liothyronine, dosed either for two days in a row per week or dosed on separate days for no more than 3 days per week at about 5.0 μg to about 10.0 μg.

In various embodiments, the methods may include administering an effective amount of a combination of one or more mTOR inhibitors with an effective amount of one or more thyroid hormones and an effective amount of a PDE5 inhibitor. In various embodiments, the methods may include administering an effective amount of one or more mTOR inhibitors with an effective amount of one or more thyroid hormones, an effective amount of a flavonoid and an effective amount of a PDE5 inhibitor. In various embodiments, the methods may include administering an effective amount of one or more mTOR inhibitors with an effective amount of one or more thyroid hormones and an effective amount of a high dose of a flavonoid, which is associated with a senolytic effect, and an effective amount of a PDE5 inhibitor.

In various embodiments, the methods may include administering the effective amount of the compositions of the disclosure that may further contain additional pharmaceutically acceptable carriers, excipients, other medicinal or pharmaceutical agents, carriers, adjuvants, etc.

In various embodiments, the methods may include administering the effective amount of the compositions to a patient through any suitable route of administration effective in delivering an amount of active agent or active agents to a patient. Suitable routes of administration include oral, intravascular, intramuscular, subcutaneous, parenteral, enteral, and rectal or the like.

In various embodiments, the methods may include administering the effective amount of the compositions comprised of each of the ingredients in a single administration form, such as a pill, tablet, capsule, oral solution, injection solution, infusion solution, or any of the forms described herein. In various embodiments, the methods may include administering the effective amount of the compositions from a kit comprising each of the individual ingredients, together with instructions for administering each ingredient. In some forms of the kit, certain ingredients will already be combined such that one, two, three, four, or more of the components or ingredients of the composition are in a single administration form as described herein.

EXAMPLE

Clinical Study of Metformin and Icosapent Ethyl 50 to 100 patients having a BMI of 27.3 and above are recruited for study. 50 patients are further recruited for a control group. Weight changes are monitored among the patients. Half of the patients with a BMI of 27.3 and above are administered a combination of metformin and icosapent ethyl. The remaining patients with a BMI of 27.3 and above are administered icosapent ethyl and metformin in combination with a vitamin combination. All patients are administered a low-fat diet.

A baseline weight is logged for each patient at initiation of the study. Weight changes are assessed every 3 months thereafter for 1 year. At the end of 1 year, overall weight loss is assessed.

This written description uses examples to disclose the subject matter herein, including the best mode, and also to enable any person skilled in the art to practice the subject matter disclosed herein, including making and using any devices or systems and performing any incorporated methods. The patentable scope of the disclosure is defined by the claims, and may include other examples that occur to those skilled in the art. Such other examples are intended to be within the scope of the claims if they have structural elements, that do not differ from the literal language of the claims, or if they include equivalent structural elements with insubstantial differences from the literal languages of the claims.

What is claimed is:

1. A method of treating obesity comprising administering an effective amount of a pharmaceutical composition comprising icosapent ethyl and metformin.

2. The method of claim 1, wherein the pharmaceutical composition further comprises an effective amount of one or more active agents selected from the group consisting of: vitamin B derivatives, quercetin, resveratrol, NAD+, PDE5 inhibitors, cholesterol-lowering agents, one or more additional mammalian target of rapamycin (mTOR) inhibitors selected from the group consisting of a flavonoid, a macrolide and any combinations thereof.

3. The method of claim 1, wherein the pharmaceutical composition further includes one or more active agents selected from the group consisting of quercetin, cholesterol-lowering agents, and combinations thereof.

4. The method of claim 2, wherein the flavonoid is selected from the group consisting of fisetin and fisetin derivatives.

5. The method of claim 2, wherein the macrolide is rapamycin.

6. The method of claim 2, wherein the pharmaceutical composition further comprises an effective amount of one or more thyroid hormones.

7. The method of claim 6, wherein the one or more thyroid hormones include liothyronine.

8. The method of claim 2, wherein the flavonoid is selected from the group consisting of fisetin and fisetin derivatives.

* * * * *